US00PP29346P3

(12) United States Plant Patent
Monge

(10) Patent No.: US PP29,346 P3
(45) Date of Patent: May 29, 2018

(54) ***SANSEVIERIA* PLANT NAMED 'BLACK PRINCESS SANDY'**

(50) Latin Name: *Sansevieria trifasciata*
Varietal Denomination: BLACK PRINCESS SANDY

(71) Applicant: Luis Carlos Monge, Pavones (CR)

(72) Inventor: Luis Carlos Monge, Pavones (CR)

(73) Assignee: Fleurizon, LLC, Camarillo, CA (US)

( * ) Notice: Subject to any disclaimer, the term of this patent is extended or adjusted under 35 U.S.C. 154(b) by 0 days. days.

(21) Appl. No.: 15/330,521

(22) Filed: Sep. 30, 2016

(65) Prior Publication Data

US 2018/0098476 P1 Apr. 5, 2018

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
See application file for complete search history.

*Primary Examiner* — Susan McCormick Ewoldt
(74) *Attorney, Agent, or Firm* — Cassandra Bright

(57) ABSTRACT

A new and distinct *Sansevieria* cultivar named 'BLACK PRINCESS SANDY' is disclosed, characterized by uniquely pliable foliage and plants that produce many leaves and sucker abundantly. Foliage is dark green with lighter greyed-green striations. The new variety is a *Sansevieria*, typically produced as an indoor ornamental plant.

1 Drawing Sheet

Latin name of the genus and species: *Sansevieria trifasciata.*

Variety denomination: 'BLACK PRINCESS SANDY'.

BACKGROUND OF THE INVENTION

This application relates to a new cultivar of *Sunsevieria trifasciata*. The new variety is the product of chance discovery. The inventor discovered the new variety as a whole plant, naturally occurring mutation from the parent plant *Sansevieria trifasciata* 'Zeylanica'.

The new variety was first observed by the inventor, in 2012 in a planting of the parent plants, at a commercial nursery in Costa Rica. After identifying the new variety as a potentially interesting selection, the inventor continued confidential testing and propagation of 'BLACK PRINCESS SANDY', assessing stability of the unique characteristics of this variety.

Asexual reproduction of the new cultivar 'BLACK PRINCESS SANDY' was first performed at a commercial nursery in Costa Rica by leaf cuttings of original plant in 2012. Through subsequent propagation, approximately 5 generations have been reproduced, which have shown that the unique features of this cultivar are stable and reproduced true to type.

SUMMARY OF THE INVENTION

The cultivar 'BLACK PRINCESS SANDY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLACK PRINCESS SANDY.' These characteristics in combination distinguish 'BLACK PRINCESS SANDY' as a new and distinct *Sansevieria* cultivar:

1. Foliage of the new variety is uniquely flexible. Foliage bends easily and resists breakage.
2. Foliage is very dark Green, with light and dark greyed-green horizontal striations.
3. Plants produce more leaves per plant on average and suckers abundantly.
4. Acute leaf.
5. Large leaf *Sanseviera* variety.

PARENT COMPARISON

Plants of the new cultivar 'BLACK PRINCESS SANDY' are similar to the parent variety, in many horticultural characteristics. However the new variety, 'BLACK PRINCESS SANDY' differs from parent in the following characteristics:

1. The parent variety does not have pliable leaves resistant to breakage, as found in the new variety.
2. Foliage of the new variety is narrower in width.
3. The new variety has less light colored striations.
4. Plants of the new variety produce more leaves per plant than the parent variety.
5. Foliage of the new variety is more acute than that of the parent variety.

COMMERCIAL COMPARISON

There is no similar variety but 'BLACK PRINCESS SANDY' can be compared with the unpatented commercial variety *Sanservieria*. 'Black Coral', unpatented. However the new variety, 'BLACK PRINCESS SANDY' differs from 'Black Coral' in the following characteristics:

1. Foliage of the new variety is more pliable and resistant to breakage then foliage of the comparator.

2. Foliage of the new variety is darker green, with less light colored striations.
3. Foliage of the new variety has a more acute shape than that of the comparator.
4. Plants of the new variety produce more leaves per plant than 'Black Coral'.
5. Plants of the new variety are shorter than plants of 'Black Coral'.

BRIEF DESCRIPTION OF THE PHOTOGRAPH

The accompanying photograph in FIG. 1 illustrates in full color a typical plant of 'BLACK PRINCESS SANDY' grown in a commercial greenhouse in Costa Rica. The plant was grown in the ground.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BLACK PRINCESS SANDY' plant is grown in Florida. The plant is approximately 5 months old in a 6 inch pot. Temperatures ranged between 22° C. to 40° C. during the day and 15° C. to 30° C. at night. No chemical treatments were given to the plants. Measurements and numerical values represent averages of typical plant types.

Botanical classification: *Sansevieria trifasciata* 'BLACK PRINCESS SANDY'.

Propagation:

*Time to initiate rooting*.—About 2 to 3 months at approximately 17° C. to 40° C.

*Root description*.—Moderately thick, slightly fleshy, slightly fibrous, moderately dense, moderately branched, colored greyed-orange, near RHS N170B.

Plant:

*Growth habit*.—Monopodial, irregular rosulate.

*Growth rate*.—Slightly faster than moderate.

*Height*.—Approximately 30 to 40 cm.

*Plant spread*.—Approximately 15 cm.

*Growth rate*.—Moderate. Approximately 5 to 6 months to a commercially finished plant.

*Number of leaves per plant at 5 to 6 month*.—Average range: 22 to 30.

Foliage:

*Leaf*.—Arrangement: Rosulate. Average Length: Average 35 cm. Average Width: Average 4.0 cm. Depth (thickness) of Leaf blade: Approximately 3 mm to 5 mm slightly succulent. Shape of blade: Ensiform. Blade aspect: Moderate inward fold. Oldest foliage slightly undulate. Growth Aspect: Leaves grow completely upright. Apex: Sharply acute. Base: Decurrent. Margin: Entire. Texture of top surface: Glabrous. Texture of bottom surface: Glabrous. Appearance of top surface: Matte. Appearance of bottom surface: Matte. Color: Young foliage upper side: Darker than 136A. Wavy striations colored near Greyed-Green 189C. Low density of striations, approximately 20 to 30% of leaf is the lighter color. Young foliage under side: Darker than 136A. Wavy striations colored near Greyed-Green 189C. Low density of striations, approximately 20 to 30% of leaf is the lighter color. Mature foliage upper side: Darker than 136A. Wavy striations colored near Greyed-Green 189C and Green 138C. Low density of striations, approximately 30 to 40% of leaf is the lighter color. Mature foliage under side: Darker than 136A. Wavy striations colored near Greyed-Green 189C and 138C. Low density of striations, approximately 30% of leaf is the lighter color. Venation: Type: Parallel. Color: Upper side: Indistinguishable from leaf blade. Under side: Indistinguishable from leaf blade.

*Sheath*.—Average Length: Approximately 2.5 cm. Average Width: Approximately 4 cm(clasping leaf base). Color: Near Green 138C. Texture: Glabrous, moderately glossy. Other: Thin, papery sheath occurs under the soil.

*Other distinguishing characteristics*.—Leaf is very pliable, resists breakage.

Other characteristics:

*Disease resistance*.—Neither resistance nor susceptibility to the normal diseases found in *Sansevieria* has been observed.

*Fruit/seed production*.—No fruits/seeds detected to date.

What is claimed is:

1. A new and distinct cultivar of *Sansevieria* plant named 'BLACK PRINCESS SANDY' as herein illustrated and described.

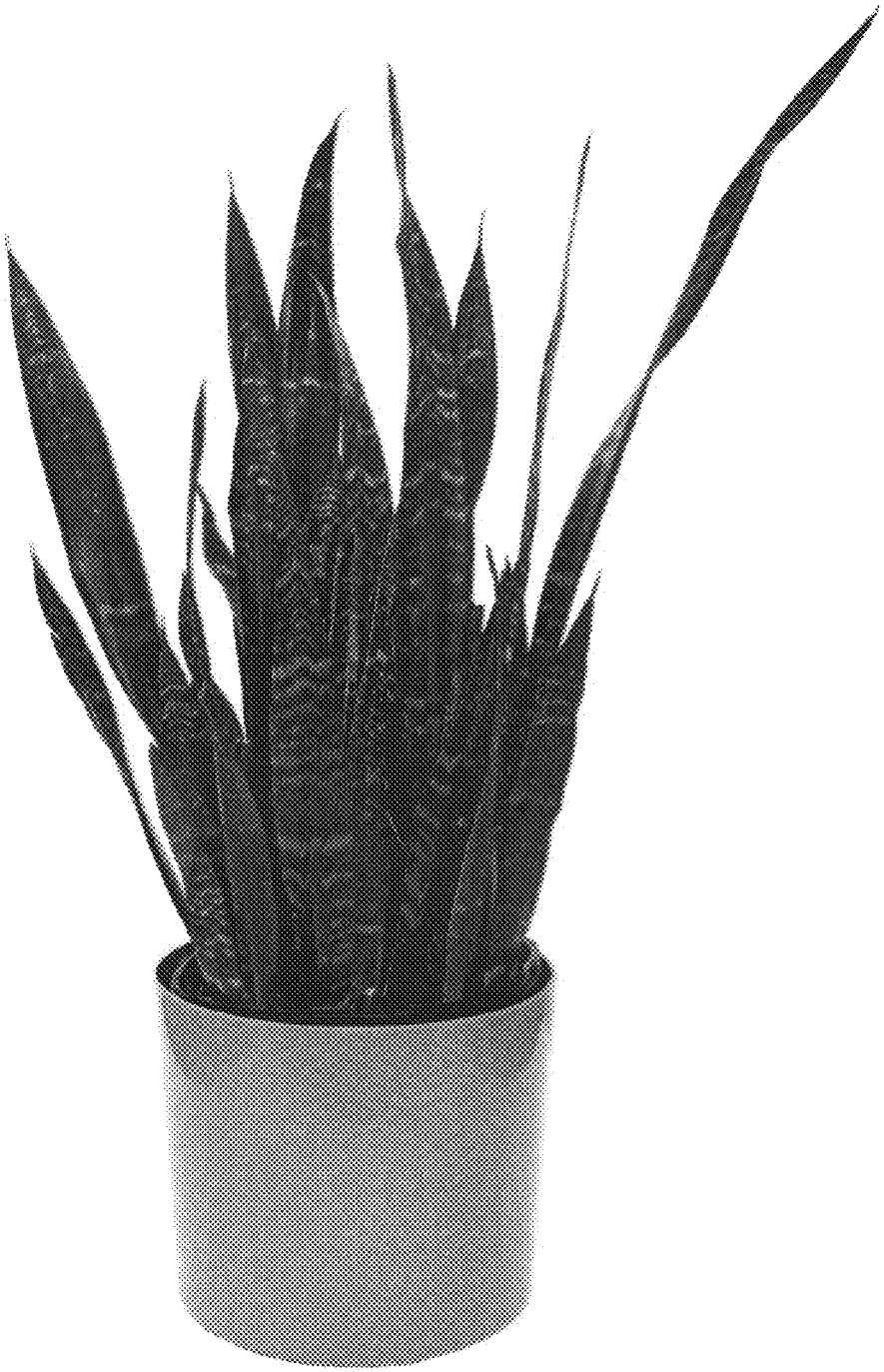

* * * * *